United States Patent [19]

Aburaki et al.

[11] Patent Number: 5,696,096
[45] Date of Patent: Dec. 9, 1997

[54] PRADIMICIN DERIVATIVES

[75] Inventors: Shimpei Aburaki, Kawasaki; Haruhiro Yamashita, Chiba; Takayuki Naito, Kawasaki, all of Japan

[73] Assignee: Bristol-Myers Squibb Company, Princeton, N.J.

[21] Appl. No.: 590,621

[22] Filed: Sep. 28, 1990

[51] Int. Cl.$^6$ .................... A61K 31/70; C07H 15/24
[52] U.S. Cl. ................. 514/33; 514/25; 514/27; 536/6.4; 536/17.2; 536/16.8; 536/18.1
[58] Field of Search ................ 536/18.1, 16.8, 536/6.4, 17.2; 514/25, 17, 33

[56] References Cited

U.S. PATENT DOCUMENTS

| | | | |
|---|---|---|---|
| 4,130,709 | 12/1978 | Nagarajan | 536/16.8 |
| 4,870,165 | 9/1989 | Oki et al. | 536/6.4 |
| 4,960,755 | 10/1990 | Nishio et al. | 514/8 |
| 4,973,673 | 11/1990 | Sawada | 536/6.4 |

FOREIGN PATENT DOCUMENTS

| | | |
|---|---|---|
| 315147 | 10/1989 | European Pat. Off. . |
| 345735 | 12/1989 | European Pat. Off. . |

*Primary Examiner*—Elli Peselev
*Attorney, Agent, or Firm*—Thomas R. Savitsky

[57] ABSTRACT

The present invention relates to new antifungal compounds having the formula

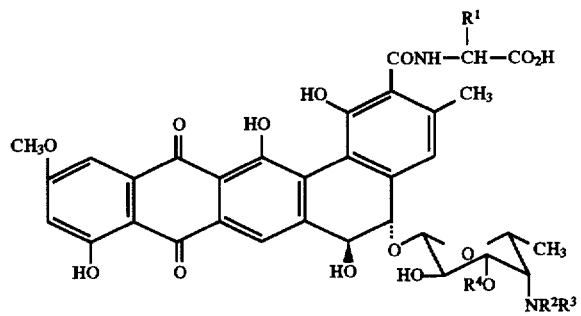

wherein $R^1$ is hydrogen, methyl, or hydroxymethyl; $R^2$ and $R^3$ are independently selected from the group consisting of hydrogen and $C_{1-5}$ alkyl; and $R^4$ is selected from the group consisting of β-L-xylosyl, β-D-ribosyl, α-L-arabinosyl, β-D-chinovosyl, β-D-fucosyl, and β-D-glucosyl; with the proviso that when $R^1$ is methyl or hydroxymethyl, and one of $R^2$ or $R^3$ is methyl, $R^4$ is not β-D-glucosyl; or a pharmaceutically acceptable salt thereof.

10 Claims, No Drawings

PRADIMICIN DERIVATIVES

BACKGROUND OF THE INVENTION

1. Field of the Invention

The present invention relates to novel antifungal compounds, methods for making and using the same, and pharmaceutical compositions containing them. More particularly, the compounds of the invention are semi-synthetic pradimicin derivatives.

2. Background Art

Pradimicins, formerly called BU-3608 antibiotics, are a family of broad spectrum antibiotics active against pathogenic yeasts and fungi. A number of pradimicin compounds obtained by fermentation of *Actinomadura hibisca* have been reported, and their structures are shown below as formula (I):

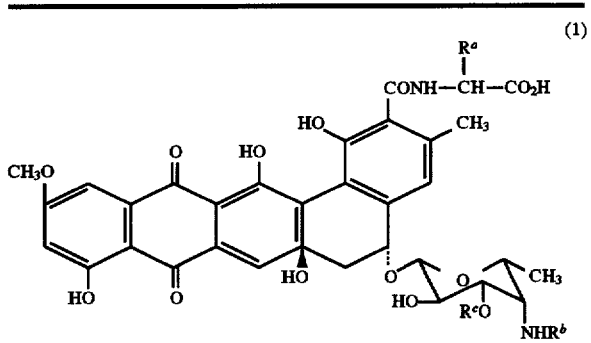

| Pradimicin | $R^a$ | $R^b$ | $R^c$ |
|---|---|---|---|
| A | $CH_3$ | $CH_3$ | β-D-Xylosyl |
| B | $CH_3$ | $CH_3$ | H |
| C | $CH_3$ | H | β-D-Xylosyl |
| D | H | $CH_3$ | β-D-Xylosyl |
| E | H | H | β-D-Xylosyl |
| FA-1 | $CH_2OH$ | $CH_3$ | β-D-Xylosyl |
| FA-2 | $CH_2OH$ | H | β-D-Xylosyl |

U.S. Pat. No. 4,870,165 discloses pradimicins A, B, and C. Pradimicin C is identical to benanomicin B disclosed in European Patent Application No. 315,147 (published May 10, 1989).

European Patent Application No. 345,735 (published Dec. 13, 1989) discloses pradimicins D, E, and their respective desxylosyl derivatives.

European Patent Application No. 351,799 (published Jan. 24, 1990) discloses N-alkylated derivatives of pradimicins A, B, C, D, and E.

European Patent Application No. 368,349 (published May 16, 1990) discloses pradimicins FA-1, FA-2, their respective desxylosyl derivatives, and N-alkylated derivatives thereof.

It will be noted that heretofore reported pradimicins possess either a monosaccharide moiety (in formula I, the amino sugar in which $R^c$ is hydrogen) or a disaccharide moiety consisting of the amino sugar and β-D-xylose linked thereto. The compounds of the present invention differ from the known pradimicins in having a sugar moiety other than D-xylosyl attached to the amino sugar. These novel compounds are also active antifungal agents.

SUMMARY OF THE INVENTION

The present invention provides compounds having formula (II)

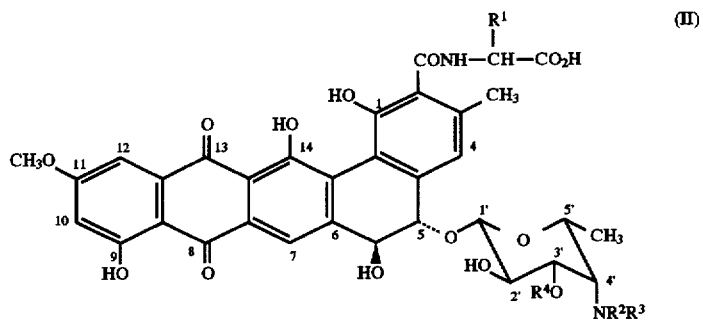

wherein $R^1$ is selected from the group consisting of hydrogen, methyl, and hydroxymethyl; $R^2$ and $R^3$ are independently hydrogen or $C_{1-5}$ alkyl; and $R^4$ is selected from the group consisting of β-L-xylosyl, β-D-ribosyl, α-L-arabinosyl, β-D-chinovosyl (6-deoxy-β-D-glucosyl), β-D-glucosyl, and β-D-fucosyl, with the proviso that when $R^1$ is methyl or hydroxymethyl and one of $R^2$ or $R^3$ is methyl, $R^4$ is not β-D-glucosyl; or a pharmaceutically acceptable salt thereof.

Another aspect of the invention provides a method for treating a mammalian host infected with a susceptible pathogen which comprises administering to said host an antifungal effective amount of a compound of formula (II).

Yet another aspect of the invention provides a pharmaceutical composition which comprises a compound of formula (II) and a pharmaceutically acceptable carrier.

DETAILED DESCRIPTION OF THE INVENTION

For compounds of formula (II) in which $R^1$ represents a methyl or a hydroxymethyl group, the resulting amino acid residue is D-alanine or D-serine, respectively. The term "alkyl" used herein encompasses straight and branched carbon chains. "Pharmaceutically acceptable salt" includes acid addition salts formed with inorganic acids, such as hydrochloric acid, sulfuric acid, phosphoric acid, nitric acid, and the like, or with organic acids, such as acetic acid, citric acid, fumaric acid, lactic acid, tartaric acid, and the like; base salts formed with inorganic bases, such as sodium hydroxide, potassium hydroxide, sodium carbonate, calcium carbonate, magnesium hydroxide, and the like, or with organic bases, such as diethylamine, ethylenediamine, triethylamine, ethanolamine, and the like; and internal salt providing the zwitterion. "Desxylosylpradimicin" refers to a compound of formula (I) in which the β-D-xylosyl group has been replaced by hydrogen, and includes pradimicin B. The abbreviation "CBZ" refers to the benzyloxycarbonyl radical.

A preferred embodiment of the present invention provides compounds of formula (II) wherein $R^1$ is methyl. Another preferred embodiment provides compounds of formula (II) wherein one of $R^2$ and $R^3$ is hydrogen and the other is a methyl group. A more preferred embodiment provides compounds of formula (II) wherein $R^1$ is methyl, and one of $R^2$ and $R^3$ is hydrogen and the other is methyl.

The compounds of the present invention may be prepared by condensing an appropriately protected desxylosylpradimicin with an appropriately protected sugar under conventional glycosidation conditions. The protecting groups are then removed to afford the end products. A suitable reaction sequence is depicted below in Scheme I.

The primary amino group of desxyloslypradimicins C, E and FA-2 may be converted to a secondary amine by reductive alkylation. The desxylosylpradimicin is reacted with an aldehyde or ketone having from 1 to 5 carbon atoms, preferably from 1 to 3 carbon atoms, e.g., formaldehyde, acetaldehyde, propionaldehyde, and acetone, followed by reduction of the imine thus formed. The carbonyl compound is used in about equimolar amount relative to the desxylosylpradimicin; and in order to optimize formation of the secondary amine, desxylosylpradimicin is preferably used in excess relative to the carbonyl compound. The reducing agent may be, for example, sodium borohydride, sodium cyanoborohydride, and lithium aluminum hydride. The reaction is carried out in an appropriate solvent, such as water,

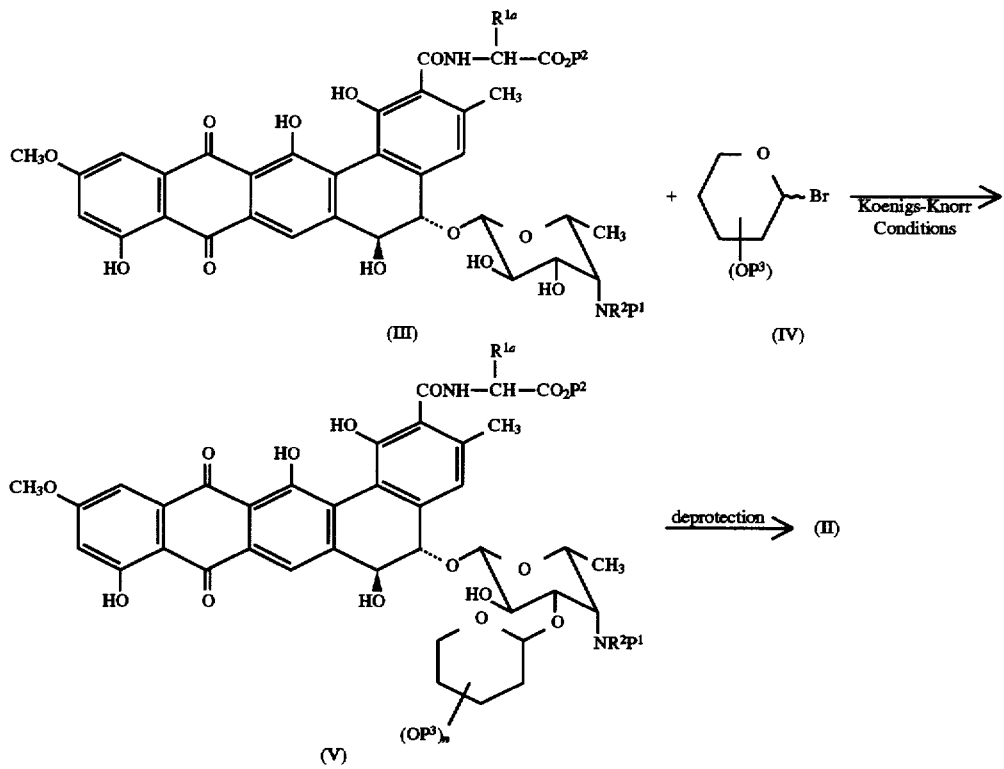

In the above scheme, $R^{1a}$ is hydrogen, methyl, or protected hydroxymethyl; $R^2$ is hydrogen or $C_{1-5}$ alkyl; $P^1$ is $C_{1-5}$ alkyl or an amino protecting group; $P^2$ and $P^3$ are carboxyl and hydroxyl protecting groups, respectively; and n is 3 or 4.

Compounds of formula (III) may be prepared from their corresponding desxylosylpradimicins, which in turn are obtained from pradimicins of formula (I) upon treatment with a mineral acid at elevated temperature for a sufficient time to allow cleavage of the xylosyl group. Thus, for example, heating pradimicin A in the presence of hydrochloric acid at 80° C. for 7 hours provides pradimicin B (i.e., desxylosylpradimicin A); desxylosylpradimicins C, D, E, FA-1 and FA-2 may be prepared by similar processes. Desxylosylpradimicins C, D, and E and their preparation are disclosed in European Patent Application No. 351,799; desxylosylpradimicins FA-1 and FA-2 and their preparation are disclosed in European Patent Application No. 368,349. The disclosures of these applications are hereby incorporated by reference.

acetonitrile, lower alkanols, dimethyl sulfoxide, tetrahydrofuran, or a mixture thereof, at a temperature conducive to product formation, generally from about 20° to about 100° C., for a period of time sufficient to substantially complete the reaction.

It will be appreciated that in the above-described reductive alkylation, a tertiary amine having two identical alkyl substituents may be obtained if the carbonyl compound is used in at least two molar equivalents relative to the desxylosylpradimicin. Desxylosylpradimicin A, D and FA-1, which have a secondary amino group, may be used as starting material to prepare tertiary amines having two methyl groups or two different alkyl substituents, one of which being a methyl group. Other tertiary amines having two different alkyl substituents may be prepared by reacting, in a similar fashion, the firstly obtained secondary amine with a second carbonyl compound different from the first one.

The N-alkylation reaction described above may also be accomplished after the glycosidation reaction. The order in which the steps are performed is not particularly critical.

The primary and secondary amines may be protected by acylation or formation of urethane-type derivative, e.g., with benzyl chloroformate. The free carboxyl group may be blocked by formation of esters with a lower alkanol, e.g., methanol and ethanol. In the case of desxylosylpradimicins FA-1 and FA-2, the primary hydroxyl group can be suitably protected by acylation with a carboxylic acid, e.g., acetic acid, benzoic acid, and the like. It will be appreciated that the protecting groups used are not particularly critical, and the selection of the protecting groups and methods for introducing them are well within the skills of a person skilled in the art.

The compounds of formula (IV) are obtained from the corresponding 1-O-acetate sugar when treated with hydrobromic acid in acetic acid.

The condensation between compounds of formulas (III) and (IV) may be carried out under standard Koenigs-Knorr conditions. Typically, a protected glycosyl halide, e.g., a peracetylated glycosyl bromide is used, and the reaction is carried out under anhydrous conditions in an inert organic solvent, such as methylene chloride, chloroform, 1,2-dichloroethane, dioxane, and the like. Anhydrous conditions may be maintained by including in the reaction mixture a dehydrating agent, such as molecular sieves. The reaction mixture also contains a silver or mercuric salt, such as mercuric cyanide or mercuric bromide. Glycosidation reaction is preferably carried out at an elevated temperature, and for a period of time, sufficient to substantially convert the starting materials into the reaction product. Generally, reaction between desxylosylpradimicin starting material (III) and the sugar at about 60°–100° C. is satisfactorily complete in about 2–24 hours.

The glycosidation affords the desired compound, 3'-O-coupling product of formula (V). In the case of coupling with D-glucose, two other products are also produced in addition to the expected desired product. The two coupling products have been determined to result from attachment to the 1-O- site, and their structures are shown as formulas (VI) and (VII). These side products can be separated from the desired product by chromatographic methods.

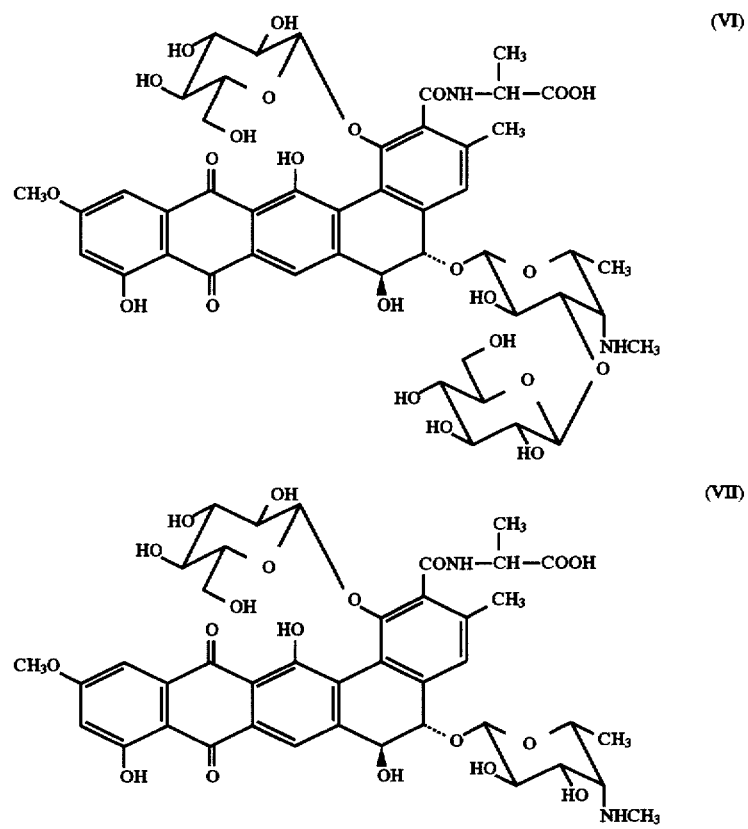

The protecting groups of compounds of formula (V) are then removed to provide compounds of the present invention. The choice for deblocking method depends on the nature of the protecting groups; for example, the various ester linkages may be cleaved by hydrolysis under alkaline conditions; the benzyloxycarbonyl protecting group may be removed by catalytic hydrogenation.

BIOLOGICAL ACTIVITY

Antifungal activities of representative compounds of the present invention were evaluated in vitro. The minimum inhibitory concentrations (MICs) against various fungi were determined by serial agar dilution method using Sabouraud dextrose agar. Thus, approximately 0.003 ml of fungal suspension containing $10^6$ cells/ml was applied to the surface of agar plates containing the test antibiotics. The MIC values recorded after the cultures had been incubated for 40 hours at 28° C. are set forth below in Table 1.

TABLE 1

In vitro Antifungal Activity of Pradimicin B Derivatives

| Compound | MIC (μg/ml) | | | |
|---|---|---|---|---|
| | Candida albicans | Cryptococcus neoformans | Aspergillus fumigatus | Trichophyton mentagrophytes |
| Pradimicin A | 50.0 | 0.8 | 1.6 | 1.6 |
| Example 1 | 50.0 | 1.6 | >100.0 | >100.0 |
| Example 2 | >25.0 | 1.6 | 12.5 | 25.0 |
| Example 3 | 6.3 | 1.6 | 6.3 | 6.3 |
| Example 4 | 25.0 | 1.6 | 3.1 | 1.6 |
| Example 5 | 6.3 | 1.6 | 3.1 | 1.6 |
| Example 6 | 12.5 | 1.6 | 3.1 | 3.1 |
| Pradimicin B | 3.1 | 0.8 | 6.3 | 6.3 |

For treatment of fungal infections in animals and human beings, the antibiotics of the present invention may be given in an antifungally effective amount by any accepted routes of administration; these include, but are not limited to, intravenous, intramuscular, oral, intranasal, and for superficial infections, topical administration. Preparations for parenteral administration include sterile aqueous or nonaqueous solutions, suspensions, or emulsions. They may also be manufactured in the form of sterile solid compositions which can be dissolved in sterile water, physiological saline, or some other sterile injectable medium immediately before use. Oral formulation may be in the form of tablets, gelatin capsules, powders, lozenges, syrups, and the like. For topical administration, the compound may be incorporated into lotions, ointments, gels, creams, salves, tinctures, and the like. Unit dosage forms may be prepared using methods generally known to those skilled in the art of pharmaceutical formulations.

It will be appreciated that, when treating a host infected with a fungus susceptible to the antibiotics of this invention, the actual preferred route of administration and dosage used will be at the discretion of the attending clinician skilled in the treatment of fungal infections and will vary according to the causative organism, its sensitivity to the antibiotic, severity and site of the infection, and patient characteristics, such as age, body weight, rate of excretion, concurrent medications, and general physical condition.

The following examples are illustrative without limiting the scope of the present invention.

Preparation of 4'-N-Benzyloxycarbonylpradimicin B Methyl Ester

A. Preparation of Pradimicin B

A mixture of pradimicin A sodium salt (6 g, 7 mmol), acetic acid (240 ml), and 2N HCl (240 ml) was stirred at 80° C. for 7 hours. The solvent was then evaporated and the residual oil dissolved in water. The solution was absorbed on μBondapak $C_{18}$ column (400 ml), and the column was washed with water and eluted with 25% aqueous acetonitrile (adjusted to pH 3.5 with 1N HCl). Fractions containing the desired product were collected and evaporated to give pradimicin B (3.25 g, 62% yield, purity 85% by HPLC). This product was used in the following benzyloxycarbonylation without further purifications.

MP 140° C. IR $v_{max}$ (KBr) cm$^{-1}$: 3400, 1720, 1600. UV $\lambda_{max}^{(0.01N-NaOH)}$ nm ($E_{1cm}^{1\%}$): 319 (189), 498 (183).

$^1$H NMR (DMSO-d$_6$) δ: 1.27 (3H, d, J=6.4 Hz, 5'-Me) 1.33 (3H, d, J=7.3 Hz, 17-Me), 2.31 (3H, s, 3-Me), 2.69 (3H, s, 4'-NMe), 3.88 (1H, q, 5'-H), 4.40 (1H, dq, $J_{17,NH}=J_{17,17}$-Me=7.3 HZ, 17-H), ca. 4.5–4.6 (2H, m, 5- and 6-H), 4.70 (1H, m, 1'-H), 6.96 (1H, d, $J_{10,12}$=2.6 Hz, 10-H), 7.18 (1H, s, 4-H), 7.31 (1H, d, 12-H), 8.08 (1H, brs, 7-H).

B. Preparation of 4'-N-Benzyloxycarbonylpradimicin B

A mixture of pradimicin B (3.13 g, 4.2 mmol) and N,O-bis(trimethylsilyl)acetamide (20.8 ml, 84 mmol) in dry methylene chloride (150 ml) was stirred at ambient temperature for about 0.5 hour until a solution was obtained. Benzyloxycarbonyl chloride (3.0 ml, 21 mmol) was added to the above solution, and stirring was continued for 2.5 hours. The solvent was evaporated, and to the oily residue was added methanol (210 ml) and 1N HCl (42 ml), successively, under ice-water cooling. The mixture was stirred at ambient temperature for 0.5 hour, and then the solvent was evaporated. The residue was triturated with water, filtered, and washed with water and ether, successively, to yield a solid (3.32 g, yield 94%), which consisted of 4'-N-CBZ pradimicin B (65%) and its methyl ester (19%). This sample was used for the next reaction without further purifications. A part of this sample (120 mg) was purified by $C_{18}$ column using 50% aqueous acetonitrile (pH 3.5 with 1NHCl) as eluent to afford 4'-N-CBZ pradimicin B (47 mg, 90% pure by HPLC).

MP 215° C. (dec.). IR $v_{max}$ (KBr) cm$^{-1}$: 3370, 1720, 1660, 1600. UV $\lambda_{max}^{(MeOH)}$ nm ($E_{1cm}^{1\%}$): 234 (251), 291 (221), 469 (95).

$^1$H NMR (DMSO-d$_6$-D$_2$O) δ: 1.02 & 1.04 (3H, each d, J=6.4 Hz, 5'-Me), 1.32 (3H, d, J=7.3 Hz, 17-Me), 2.29 & 2.30 (3H, each s, 3-Me), 3.08 & 3.13 (3H, each s, 4'-NMe), 3.96 (3H, s, 11-OMe), 4.39 (1H, q, 17-H), 4.46 (1H, brd, $J_{5,6}$=10.3 Hz, 5-H), 4.54 (1H, brd, 6-H), 4.60 (1H, d, $J_{1',2'}$=7.3 Hz, 1'-H) 5.06 & 5 10 (2H, each ABq, J=12.8 Hz, —CH$_2$Ph), 6.95 (1H, d, $J_{10,12}$=2.1 Hz, 10-H), 7.09 (1H, brs, 4-H), 7.30 (1H, d, 12-H), ca. 7.4 (5H, m, Ph), 8.08 (1H, brs, 7-H).

FAB(+)-MS (m/z): 843 (M+H).

C. Preparation of 4'-N-Benzyloxycarbonylpradimicin B Methyl Ester

Thionyl chloride (1.4 ml) and 4'-N-benzyloxycarbonylpradimicin B were added to a cold mixture of methanol (100 ml) and dry 1,2-dichloroethane (30 ml), and the mixture was stirred at ambient temperature for 3 hours. The solvents were removed, and the residue was purified by silica gel (Wakogel C-200, 450 g in CHCl$_3$) column with CHCl$_3$—CH$_3$OH (15:1, v/v) as eluent to give 4'-N-CBZ pradimicin B methyl ester (2.80 g in 86% yield) as deep red powder, 95% pure by HPLC.

MP 200°–205° C. (dec.). IR $v_{max}$ (KBr) cm$^{-1}$: 3400, 1730, 1670, 1620, 1440. UV $\lambda_{max}^{(MeOH)}$ nm ($E_{1cm}^{1\%}$): 226 (285), 280 (245), 500 (118).

$^1$H NMR (DMSO-d$_6$-D$_2$O) δ: 1.03 & 1.04 (3H, each d, J=6.9 Hz, 5'-Me), 1.32 (3H, d, J=7.3 Hz, 17-Me), 2.26 & 2.27 (3H, each s, 3-Me), 3.08 & 3.13 (3H, each s, 4'-NMe), 3.66 (3H, s, COOMe), 3.73 (1H, m, 5'-H), 3.93 (3H, s, 11-OMe), 4.44 (1H, q, 17-H), 4.50 (1H, d, $J_{5,6}$=10.9 Hz, 5-H), 4.61 (1H, d, $J_{1',2'}$=7.6 Hz, 1'-H), [5.00 & 5.12 (1H, ABq, J=12.9 Hz) and 5.10 (1H, s), —CH$_2$Ph], 6.88 (1H, brs, 10-H), 7.04 (1H, s, 4-H), 7.25 (1H, brs, 12-H), ca. 7.4 (5H, m, Ph), 7.98 (1H, s, 7-H).

FAB(+)-MS (m/z): 857 (M+H), 879 (M+Na).

EXAMPLE 1

Preparation of 3'-O-(β-L-xylopyranosyl) pradimicin B

To a suspension of 4'-N-benzyloxycarbonylpradimicin B methyl ester (400 mg, 0.47 mmol) in dry 1,2-dichloroethane (40 ml) were added molecular sieves 3A (4.0 g), Hg(CN)$_2$ (944 mg, 3.74 mmol) and HgBr$_2$ (421 mg, 1.17 mmol), and the mixture was stirred at room temperature for 2 hours. To the mixture was added 2,3,4-tri-O-acetyl-L-xylopyranosyl bromide [prepared in situ from the corresponding 1-O-acetate (742 mg, 2.34 mmol) by treating with 30% HBr in acetic acid (3.7 ml) at room temperature for 2 hours and subsequent evaporation]. The mixture was stirred at 80° C. overnight and then cooled to room temperature. The insoluble material was removed by filtration and washed with chloroform. The combined filtrate and washings were washed with saturated aqueous NaHCO$_3$ and NaCl solutions, dried over Na$_2$SO$_4$, and filtered.

The filtrate obtained above (200 ml) containing 4'-N-CBZ-3'-O-(2,3,4-tri-O-acetyl-β-L-xylopyranosyl) pradimicin B methyl ester was diluted with methanol (200 ml) and then treated with IN NaOH (20 ml). After evaporation of the solvents, the residue was dissolved in methanol (50 ml) and kept at room temperature for 2 hours. After being acidified with 1N HCl to pH 5, the mixture was stirred at room temperature for 2 hours and evaporated to dryness. The residue was chromatographed twice on C$_{18}$ reversed phase column by eluting with 45% aqueous acetonitrile containing 0.1% of 1N HCl. The fractions showing retention time 4.9 minutes [on HPLC; MeCN (A)/0.01M phosphate buffer (pH 3.5) (B)=$^{47.5}/_{52.5}$] were combined and evaporated to give 4'-N-CBZ-3'-O-(β-L-xylopyranosyl) pradimicin B (53 mg, 70% pure).

The N-protected derivative in MeOH (10 ml) and H$_2$O (1 ml) was subjected to hydrogenolysis over Pd-C (50 mg) at room temperature for 1 hour. After removal of catalyst by filtration, the filtrate was evaporated and the residue was basified with 1N NaOH, charged on a C$_{18}$ column, being washed with H$_2$O and then eluted with 50% aqueous MeCN. The eluate was evaporated and lyophilized to afford the title compound 22 mg (Y. 5.6%), purity 80% on HPLC [Retention time 6.2 minutes; MeCN/0.01M phosphate buffer (pH 3.5)=$^{35}/_{65}$].

MP>230° C. (dec.). IR $v_{max}$ (KBr) cm$^{-1}$: 3400, 1620. UV $\lambda_{max}^{(0.01N\ NaOH)}$ nm (E$_{1cm}^{1\%}$): 319 (92), 500 (108).

$^1$H NMR (DMSO-d$_6$) δ: 1.16 (3H, d, J=6.4 Hz, 5'-Me), 1.30 (3H, d, J=6.8 Hz, 17-Me), 2.22 (3H, s, 3-Me), 2.39 (3H, s, 4'-NMe), 3.85 (1H, dq, 17-H), 3.87 (3H, s, 11-OMe), 4.26 (1H, d, J$_{1'',2''}$=7.3 Hz, 1''-H), 4.37 (1H, d, J$_{5,6}$=10.3 Hz, 5-H), 4.44 (1H, d, 6-H), 4.55 (1H, d, J$_{1',2'}$=7.7 Hz, 1'-H), 6.64 (1H, br s, 10-H), 6.92 (1H, s, 4-H), 7.07 (1H, br s, 12-H), 7.37 (1H, d, J=6.0 Hz, 16-NH), 7.69 (1H, s, 7-H).

FAB(+)-MS m/z: 841 (M+H).

EXAMPLE 2

Preparation of 3'-O-(β-D-Ribopyranosyl)-pradimicin B

To a suspension of 4'-N-benzyloxycarbonylpradimicin B methyl ester (500 mg, 0.58 mmol) in dry 1,2-dichloroethane (50 ml) were added molecular sieves 3A (5.0 g), Hg(CN)$_2$ (1.18 g, 4.67 mmol), and HgBr$_2$ (526 mg, 1.46 mmol), and the whole mixture was stirred at room temperature for 2 hours. To the mixture obtained above was added 2,3,4-tri-O-acetyl-D-ribopyranosyl bromide, prepared in situ from its corresponding 1-O-acetate (1.11 g, 3.5 mmol) by treating with 30% HBr-AcOH (6 ml) at room temperature for 2 hours, followed by evaporation. The whole mixture was stirred at 80° C. overnight. After being cooled to room temperature, the insoluble matters were removed by filtration and washed with CHCl$_3$. The combined filtrate and washings were washed with saturated aqueous NaHCO$_3$ and NaCl solutions, dried over Na$_2$SO$_4$, and filtered.

The filtrate obtained above (ca. 200 ml) was diluted with MeOH (200 ml) and then treated with 1N NaOH (20 ml). After evaporation of the solvents, the residue was dissolved in MeOH (50 ml) and kept at room temperature for 2 hours. After being acidified with 1N HCl to pH 5, the mixture was stirred at room temperature for 2 hours and evaporated to dryness. The residue was chromatographed twice on C$_{18}$ reversed phase column by eluting with 50% aqueous acetonitrile containing 0.1% of 1N HCl. The fractions showing retention time 4.8 minutes [on HPLC; A/B=$^{50}/_{50}$] were combined and evaporated to give the 4'-N-CBZ-3'-O-(β-D-ribopyranosyl)pradimicin B (54 mg, 80% pure).

The N-protected derivative obtained above in MeOH (20 ml) and H$_2$O (2 ml) was subjected to hydrogenolysis over Pd-C (30 mg) at room temperature for 1 hour. After removal of the catalyst by filtration, the filtrate was evaporated and the residue was basified with 1N NaOH, charged on C$_{18}$ column, being washed with H$_2$O, and then eluted with 50% aqueous MeCN. The eluate was evaporated and lyophilized to afford the title compound 19 mg (Y. 3.9%), purity 80% on HPLC [Retention time 6.0 minutes; A/B=$^{30}/_{70}$].

MP>230° C. (dec.). IR $v_{max}$ (KBr) cm$^{-1}$: 3400, 1600. UV $\lambda_{max}^{(0.01N\ NaOH)}$ nm (E$_{1cm}^{1\%}$): 318 (154), 498 (164).

$^1$H NMR (DMSO-d$_6$) δ: 1.21 (3H, d, J=6.8 Hz, 5'-Me), 1.33 (3H, d, J=7.3 Hz, 17-Me), 2.26 (3H, s, 3-Me), 2.56 (3H, s, 4'-NMe), 3.90 (3H, s, 11-OMe), 4.35 (1H, m, 17-H), 4.43 (1H, d, J=10.3 Hz, 5-H), 4.48 (1H, d, 6-H), 4.68 (1H, d, J$_{1',2'}$=7.7 Hz, 1'-H), 4.89 (1H, d, J$_{1'',2''}$=5.1 Hz, 1''-H), 6.71 (1H, d, J$_{10,12}$=2.6 Hz, 10-H), 6.88 (1H, s, 4-H), 7.12 (1H, d, 12-H), 7.67 (1H, s, 7-H), ca. 8.7 (1H, brd, NH).

FAB(+)-MS m/z: 841 (M+H).

EXAMPLE 3

Preparation of 3'-O-(α-L-Arabinopyranosyl) pradimicin B

To a suspension of 4'-N-benzyloxycarbonylpradimicin B methyl ester (500 mg, 0.58 mmol) in dry 1,2-dichloroethane (50 ml) were added molecular sieves 3A (5.0 g), Hg(CN)$_2$ (1.18 g, 4.67 mmol), and HgBr$_2$ (526 mg, 1.46 mmol), and the whole mixture was stirred at room temperature for 2 hours. To the mixture obtained above was added 2,3,4-tri-O-acetyl-L-arabinopyranosyl bromide, prepared in situ from its corresponding 1-O-acetate (557 mg, 1.75 mmol) by treating with 30% HBr-AcOH (3 ml) at room temperature for 2 hours, followed by evaporation. The whole mixture was stirred at 80° C. overnight. After being cooled to room temperature, the insoluble matters were removed by filtration and washed with CHCl$_3$. The combined filtrate and washings were washed with saturated aqueous NaHCO$_3$ and NaCl solutions, dried over Na$_2$SO$_4$, and filtered.

The filtrate obtained above (200 ml) was diluted with MeOH (200 ml) and then treated with 1N NaOH (20 ml). After evaporation of the solvents, the residue was dissolved in MeOH (50 ml) and kept at room temperature for 2 hours. After being acidified with 1N HCl to pH 5, the mixture was stirred at room temperature for 2 hours and evaporated to dryness. The residue was chromatographed twice on C$_{18}$ reversed phase column by eluting with 50% aqueous acetonitrile containing 0.1% of 1N HCl. The fractions showing retention time 4.9 minutes [on HPLC; A/B=47.5/52.5] were combined and evaporated to give 4'-N-CBZ-3'-O-(β-L-arabinopyranosyl)pradimicin B (59 mg, 80% pure).

The N-protected derivative obtained above in MeOH (10 ml) and H$_2$O (1 ml) was subjected to hydrogenolysis under H$_2$ atmosphere over Pd-C (50 mg) at room temperature for 1 hour. After removal of catalyst by filtration, the filtrate was evaporated and the residue was basified with 1N NaOH, charged on C$_{18}$ column, being washed with H$_2$O and then eluted with 50% aqueous MeCN. The eluate was evaporated and lyophilized to afford the title compound 29 mg (Y. 5.9%), purity 90% on HPLC [Retention time 5.9 minutes; A/B=30/70].

MP>230° C. (dec.). IR $\nu_{max}$ (KBr) cm$^-$: 3380, 1610, 1435. UV $\lambda_{max}^{(0.01N\ NaOH)}$ nm (E$_{1cm}^{1\%}$): 318 (176), 498 (184).

$^1$H NMR (DMSO-d$_6$) δ: 1.15 (3H, d, J=6.4 Hz, 5'-Me), 1.30 (3H, d, J=6.8 Hz, 17-Me), 2.22 (3H, s, 3-Me), 2.42 (3H, s, 4'-NMe), 3.87 (3H, s, 11-OMe), 4.37 (1H, q, J$_{1'',2''}$=6.4 Hz, 1''-H), 4.37 (1H, d, J$_{5,6}$=11.0 Hz, 5-H), 4.45 (1H, d, 6-H), 4.58 (1H, d, J$_{1',2'}$=7.3 Hz, 1'-H), 6.65 (1H, brs, 10-H), 6.91 (1H, s, 4-H), 7.07 (1H, brs, 12-H), 7.38 (1H, d, 16-NH), 7.69 (1H, s, 7-H).

FAB(+)-MS m/z: 841 (M+H).

EXAMPLE 4

Preparation of 3'-O-(6-Deoxy-β-D-glucopyranosyl) pradimicin B

To a suspension of 4'-N-benzyloxycarbonylpradimicin B methyl ester (500 mg, 0.58 mmol) in dry 1,2-dichloroethane (50 ml) were added molecular sieves 3A (5.0 g), Hg(CN)$_2$ (1.18 g, 4.67 mmol), and HgBr$_2$ (526 mg, 1.46 mmol), and the whole mixture was stirred at room temperature for 2 hours. To the mixture obtained above was added 2,3,4-tri-O-acetyl-6-deoxy-D-glucopyranosyl bromide, prepared in situ from its corresponding 1-O-acetate (800 mg, 2.41 mmol) by treating with 30% HBr-AcOH (4 ml) at room temperature for 2 hours, followed by evaporation. The whole mixture was stirred at 80° C. overnight. After being cooled to room temperature, the insoluble matters were removed by filtration and washed with CHCl$_3$. The combined filtrate and washings were washed with saturated aqueous NaHCO$_3$ and NaCl solutions, dried over Na$_2$SO$_4$, and filtered.

The filtrate obtained above (ca. 200 ml) was diluted with MeOH (200 ml) and then treated with 1N NaOH (20 ml). After evaporation of the solvents, the residue was dissolved in MeOH (50 ml) and kept at room temperature for 2 hours. After being acidified with 1N HCl to pH 2, the mixture was stirred at room temperature for 2 hours and evaporated to dryness. The residue was chromatographed twice on C$_{18}$ reversed phase column by eluting with 50% aqueous acetonitrile containing 0.1% of 1N HCl. The fractions showing retention time 4.5 minutes [on HPLC; A/B=50/50] were combined and evaporated to give 4'-N-CBZ-3'-O-(6-deoxy-β-D-glucopyranosyl)pradimicin B (55 mg, 80% pure).

The N-protected derivative obtained above in MeOH (10 ml) and H$_2$O (2 ml) was subjected to hydrogenolysis over Pd-C (25 mg) at room temperature for 1 hour. After removal of catalyst by filtration, the filtrate was evaporated and the residue was basified with 1N NaOH, charged on C$_{18}$ column, being washed with H$_2$O and then eluted with 50% aqueous MeCN. The eluate was evaporated and lyophilized to afford the title compound 16 mg (Y. 3.2%), purity 80% on HPLC [Retention time 7.0 minutes; A/B=30/70].

MP 220° C. (dec.). IR $\nu_{max}$ (KBr) cm$^{-1}$: 3400, 1620, 1600. UV $\lambda_{max}^{(0.01N\ NaOH)}$ nm (E$_{1cm}^{1\%}$): 317 (124), 498 (129).

$^1$H NMR (DMSO-d$_6$) δ: 1.17 (3H×2, d, J=6.0 Hz, 5'- and 5''-Me), 1.33 (3H, d, J=6.8 Hz, 17-Me), 2.26 (3H, s, 3-Me), 2.41 (3H, s, 4'-NMe), 3.90 (3H, s, 11-OMe), 4.27 (1H, m, 17-H), 4.37 ( 1H, d, J$_{1'',2''}$=7.3 Hz, 1''-H), 4.39 (1H, d, J$_{5,6}$=10.7 Hz, 5-H), 4.44 (1H, d, 6-H), 4.60 (1H, d, J$_{1',2'}$=7.3 Hz, 1'-H), 6.70 (1H, brs, 10-H), 6.90 (1H, s, 4-H), 7.11 (1H, brs, 12-H), 7.71 (1H, s, 7-H).

FAB(+)-MS m/z: 855 (M+H) .

EXAMPLE 5

Preparation of 3'-O-(β-D-Fucopyranosyl) pradimicin B

To a suspension of 4'-N-benzyloxycarbonylpradimicin B methyl ester (500 mg, 0.58 mmol) in dry 1,2-dichloroethane (50 ml) were added molecular sieves 3A (5.0 g), Hg(CN)$_2$ (1.18 g, 4.67 mmol), and HgBr$_2$ (526 mg, 1.46 mmol), and the whole mixture was stirred at room temperature for 2 hours. To the mixture obtained above was added 2,3,4-tri-O-acetyl-D-fucopyranosyl bromide, prepared in situ from its corresponding 1-O-acetate (1.16 g, 3.0 mmol) by treating with 30% HBr-AcOH (6 ml) at room temperature for 2 hours, followed by evaporation. The whole mixture was stirred at 80° C. overnight. After being cooled to room temperature, the insoluble matters were removed by filtration and washed with CHCl$_3$. The combined filtrate and washings were washed with saturated aqueous NaHCO$_3$ and NaCl solutions, dried over Na$_2$SO$_4$, and filtered.

The filtrate obtained above (ca. 200 ml) was diluted with MeOH (200 ml) and then treated with 1N NaOH (20 ml). After evaporation of the solvents, the residue was dissolved in MeOH (50 ml) and kept at room temperature for 2 hours. After being acidified with 1N HCl to pH 5, the mixture was stirred at room temperature for 2 hours and evaporated to dryness. The residue was chromatographed twice on C$_{18}$ reversed phase column by eluting with 50% aqueous acetonitrile containing 0.1% of 1N HCl. The fractions showing retention time 5.5 minutes [on HPLC; A/B=50/50] were combined and evaporated to give 4'-N-CBZ-3'-O-(β-D-fucopyranosyl)pradimicin B (76 mg, 80% pure).

The N-protected derivative obtained above in MeOH (20 ml) and H$_2$O (2 ml) was subjected to hydrogenolysis over Pd-C (40 mg) at room temperature for 1 hour. After removal of catalyst by filtration, the filtrate was evaporated and the residue was basified with 1N NaOH, charged on C$_{18}$ column, being washed with H$_2$O and then eluted with 50% aqueous MeCN. The eluate was evaporated and lyophilized to afford the title compound 23 mg (Y. 4.6%), purity 90% on HPLC [Retention time 7.5 minutes; A/B=30/70].

MP 215° C. (dec.). IR $\nu_{max}$ (KBr) cm$^{-1}$: 3390, 1610. UV $\lambda_{max}^{(0.01N\ NaOH)}$ nm (E$_{1cm}^{1\%}$): 320 (112), 497 (118).

$^1$H NMR (DMSO-d$_6$-D$_2$O) δ: 1.13 and 1.15 (each 3H, each d, J=6.4 and 6.8 Hz, 5'- and 5''-Me), 1.29 (3H, d, J=6.8

Hz, 17-Me), 2.21 (3H, s, 3-Me), 2.37 (3H, s, 4'-NMe), 3.86 (1H, q, J=6.8 Hz, 17-H), 4.29 (1H, d, $J_{1'',2''}$=6.8 Hz, 1''-H), 4.38 (1H, d, $J_{5,6}$=11.1 Hz, 5-H), 4.44 (1H, d, 6-H), 4.59 (1H, d, $J_{1',2}$=6.8 Hz, 1'-H), 6.68 (1H, brs, 10-H), 6.94 (1H, s, 4-H), 7.12 (1H, brs, 12-H), 7.66 (1H, s, 7-H).

FAB(+)-MS m/z: 855 (M+H).

EXAMPLE 6

Preparation of Pradimicin L (3'-O-β-D-glucopyranosylpradimicin B)

To an hour stirred suspension of 4'-N-benzyloxycarbonylpradimicin B methyl ester (1.03 g, 1.2 mmol), mercuric cyanide (2.43 g, 9.2 mmol), mercuric bromide (1.08 g, 3 mmol), and molecular sieves 3A (12 g) in dry 1,2-dichloroethane (240 ml) was added tetra-O-acetyl-α-D-glucopyranosyl bromide (1.48 g, 3 mmol), and the mixture was heated at 90° C. (bath temperature) with stirring. After 15, 21, and 84 hours, a set of mercuric cyanide (2.43 g), mercuric bromide (1.08 g), and tetra-O-acetylglucosyl bromide (1.48 g) were added, and the mixture was heated for a total of 103 hours. After the insolubles were filtered and washed with chloroform, the combined filtrates were washed with 10% aqueous NaHCO$_3$, water and brine, dried over Na$_2$SO$_4$, and evaporated in vacuo. The residual oil (5.97 g) was chromatographed on silica gel (Wakogel C-200, 100 g in toluene) column using toluene, toluene-ethyl acetate (2:1), and chloroform-methanol (10:1) as eluents. The CHCl$_3$-MeOH eluents were combined and evaporated. The residue (2.70 g) was separated by a column of silica gel (Wakogel C-200, 100 g in CHCl$_3$), eluting with chloroform-methanol (100:1, 50:1, 25:1, and 10:1) to give 2 fractions of coupling products, Fraction A (Rf 0.35 on tlc, CHCl$_3$:MeOH=25:1; deep-red powder, 283 mg) and Fraction B (Rf 0.52, orange powder, 2.03 g).

To a solution of Fraction A (270 mg) in methanol (27 ml) was added 1N-NaOH (6 ml), and the mixture was stirred at ambient temperature for 1 hour. After neutralization to pH 6.5 with 1N HCl, the mixture was diluted with water (100 ml) and the organic solvent removed by evaporation. The aqueous solution was passed on a column of Diaion HP-20 (50 ml), and the column was washed with water and eluted with 40% aqueous acetonitrile to afford a crude fraction containing 4'-N-benzyloxycarbonylpradimicin L (224 mg), which was further purified by a reversed phase column (Waters, μBondapak C$_{18}$, 55–105μ, 400 ml), eluting with 45% aqueous acetonitrile (pH 3.5 with 1N HCl) to yield semi-pure 4'-N-CBZ-pradimicin L (57 mg), purity 75% on HPLC [Retention time 9.4 minutes; A/B=⁴⁰‰]. A mixture of 4'-N-CBZ-pradimicin L (50 mg) and 10% Pd-C (20 mg) in methanol (20 ml) and water (4 ml) was hydrogenated for 2 hours. The catalyst was removed, the filtrate was evaporated, and the residue was purified on a reversed phase column (Waters, μBondapak C$_{18}$, 80 ml) with 20–25% aqueous acetonitrile (pH 3.5 with 1N HCl) as eluents to give the desired pradimicin L (12 mg, yield 1.1%) as a deep-red powder.

MP 155° C. (dec.). IR $v_{max}$ (KBr) cm$^{-1}$: 1600, 1510. UV $\lambda_{max}^{(0.01N\ NaOH)}$ nm ($E_{1cm}^{1\%}$): 216 (231), 232 (228), 320 (106), 500 (106).

$^1$H NMR (DMSO-d$_6$) δ: 1.28 (3H, d, J=6.8 Hz, 5'-CH$_3$), 1.33 (3H, d, J=7.7 Hz, 17-CH$_3$), 2.31 (3H, s, 3-CH$_3$), 2.72 (3H, brs, 4'-NCH$_3$), 3.96 (3H, s, 11-OCH$_3$), 4.40 (H, quintet, J=7.3 Hz, 17-H), 4.48 (1H, d, J=7.3 Hz, 1''-H), 4.61 (2H, brs, 5-H and 6-H), 4.80 (1H, brd, 1'-H), 6.96 (1H, d, J=2.6 Hz, 10-H), 7.11 (1H, s, OH), 7.14 (1H, s, 4-H), 7.31 (1H, d, J=2.6 Hz, 12-H), 7.36 (1H, s, OH), 8.05 (1H, s, 7-H).

FAB(+)-MS m/z: 873 (M+3H).

Purity 85% on HPLC [Retention time 17.4 minutes; A/B=²⁵/₇₅].

Fraction B, obtained above, was subjected to alkaline hydrolysis and subsequent hydrogenation according to a procedure similar to that described for Fraction A to give two 1-O-β-D-glucosylated products, i.e., compounds of formulas (VI) and (VII), whose physical properties are provided below:

Compound of Formula (VI)

MP>205° C. IR $v_{max}$ (KBr) cm$^{-1}$: 1620, 1600. UV $\lambda_{max}$ nm ($E_{1cm}^{1\%}$): In Water: 234 (225), 284 (192), 460 (94). In 0.01N HCl: 234 (244), 265 (214), 460 (10V). In 0.01 N NaOH: 260 (277), 328 (sh, 81), 519 (130).

$^1$H NMR (DMSO-d$_6$/D$_2$O) δ: 1.29 (3H, d, J=6.8 Hz, 5'-CH$_3$), 1.39 (3H, d, J=7.3 Hz, 17-CH$_3$), 2.32 (3H, s, 3-CH$_3$), 2.75 (3H, s, 4'-NCH$_3$), 3.96 (3H, s, 11-OCH$_3$), 4.04 (1H, d, J=7.7 Hz, 1'''-H), 4.49 (1H, d, J=7.3 Hz, 1''-H), 4.60 (1H, d, J=11.1 Hz, 5-H), 4.64 (1H, d, J=11.1 Hz, 6-H), 4.86 (1H, d, J=7.7 Hz, 1'-H), 6.93 (1H, d, J=2.6 Hz, 10-H), 7.28 (1H, d, J=2.6 Hz, 12-H), 7.42 (1H, s, 4-H), 8.04 (1H, s, 7-H).

FAB(+)-MS m/z: 1035 (M+3H).

Purity 85% (by HPLC).

Compound of Formula (VII)

MP>140° C. (dec.). IR $v_{max}$ (KBr) cm$^{-1}$: 1620, 1600. UV $\lambda_{max}$ nm ($E_{1cm}^{1\%}$): In Water: 234 (280), 284 (244), 460 (122). In 0.01N HCl: 234 (244), 285 (213), 460 (106). In 0.01N NaOH: 260 (244), 328 (sh, 72), 519 (112).

$^1$H NMR (DMSO-d$_6$) δ: 1.29 (3H, d, J=6.8 Hz, 5'-CH$_3$), 1.39 (3H, d, J=7.3 Hz, 17-CH$_3$), 2.33 (3H, s, 3-CH$_3$), 2.73 (3H, s, 4'-NCH$_3$), 3.83 (1H, dd, J=9.8 and 4.3 Hz, 3'-H), 3.88 (1H, q, J=6.8 Hz, 5'-H), 3.96 (3H, s, 1-OCH$_3$), 4.05 (1H, d, J=7.7 Hz, 1'''-H), 4.44 (1H, quintet, J=7.3 Hz, 17-H), 4.54 (1H, d, J=11.1 Hz, 5-H), 4.62 (1H, ddd, J=11.1, 3.8 and 0.9 Hz, 6-H), 4.74 (1H, d, J=7.3 Hz, 1'-H), 6.30 (1H, br, 3'-OH), 6.95 (1H, d, J=2.6 Hz, 10-H), 7.26 (1H, d, J=2.6 Hz, 12-H), 7.43 (1H, s, 4-H), 8.04 (1H, d, J=0.9 Hz, 7-H).

FAB(+)-MS m/z: 873 (M+3H).

Purity 60% (by HPLC).

EXAMPLE 7

The general procedure described in Examples 1–6 is repeated using the following desxylosylpradimicin and a sugar starting material selected from those described in Examples 1–6 to produce the named product of formula (II).

| Staring Material | Product |
| --- | --- |
| 4'-N-CBZ-desxylosyl-pradimicin C methyl ester | 3'-O-(β-L-xylopyranosyl) desxylosylpradimicin C |
| | 3'-O-(β-D-ribopyranosyl) desxylosylpradimicin C |
| | 3'-O-(α-L-arabinopyranosyl) desxylosylpradimicin C |
| | 3'-O-(6-deoxy-β-D-glucopyranosyl)desxylosyl-pradimicin C |
| | 3'-O-(β-D-fucopyranosyl) desxylosylpradimicin C |
| | 3'-O-(β-D-glucopyranosyl) desxylosylpradimicin C |
| N,N-dimethyldesxylosyl-pradimicin C methyl ester | N,N-dimethyl-3'-O-(β-L-xylopyranosyl) |

| Staring Material | Product |
| --- | --- |
| | desxylosylpradimicin C N,N-dimethyl-3'-O-(β-D-ribopyranosyl) |
| | desxylosylpradimicin C N,N-dimethyl-3'-O-(α-L-arabinopyranosyl) |
| | desxylosylpradimicin C N,N-dimethyl-3'-O-(6-deoxy-β-D-glucopyranosyl) |
| | desxylosylpradimicin C N,N-dimethyl-3'-O-(β-D-fucopyranosyl) |
| | desxylosylpradimicin C N,N-dimethyl-3'-O-(β-D-glucopyranosyl) |
| 4'-N-CBZ-desxylosyl-pradimicin D methyl ester | desxylosylpradimicin C 3'-O-(β-L-xylopyranosyl) desxylosylpradimicin D 3'-O-(β-D-ribopyranosyl) desxylosylpradimicin D 3'-O-(α-L-arabinopyranosyl) desxylosylpradimicin D 3'-O-(6-deoxy-β-D-glucopyranosyl)desxylosyl-pradimicin D 3'-O-(β-D-fucopyranosyl) desxylosylpradimicin D 3'-O-(β-D-glucopyranosyl) desxylosylpradimicin D |
| 19-O-acetyl-4'-N-CBZ-desxylosyl-pradimicin FA-2 methyl ester* | 3'-O-(β-L-xylopyranosyl) desxylosylpradimicin FA-2 3'-O-(β-D-ribopyranosyl) desxylosylpradimicin FA-2 3'-O-(α-L-arabinopyranosyl) desxylosylpradimicin FA-2 3'-O-(6-deoxy-β-D-glucopyranosyl)desxylosyl-pradimicin FA-2 3'-O-(β-D-fucopyranosyl) desxylosylpradimicin FA-2 3'-O-(β-D-glucopyranosyl) desxylosylpradimicin FA-2 |

*19-O- refers to the primary hydroxyl group of the serine moiety.

What is claimed is:

1. A compound having the formula

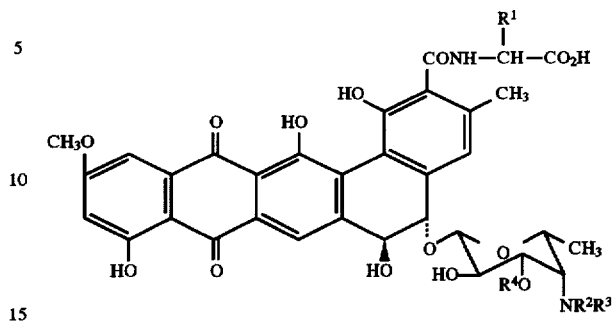

wherein $R^1$ is hydrogen, methyl, or hydroxymethyl; $R^2$ and $R^3$ are independently selected from the group consisting of hydrogen and $C_{1-5}$ alkyl; and $R^4$ is selected from the group consisting of β-L-xylosyl, β-D-ribosyl, α-L-arabinosyl, β-D-chinovosyl, β-D-fucosyl, and β-D-glucosyl; with the proviso that when $R^1$ is methyl or hydroxymethyl, and one of $R^2$ or $R^3$ is methyl, $R^4$ is not β-D-glucosyl; or a pharmaceutically acceptable salt thereof.

2. A compound of claim 1 wherein $R^1$ is methyl.

3. A compound of claim 1 wherein $R^2$ is hydrogen and $R^3$ is methyl.

4. A compound of claim 2 wherein $R^1$ is methyl, $R^2$ is hydrogen, and $R^3$ is methyl.

5. A compound of claim 4 wherein $R^4$ is β-L-xylosyl.

6. A compound of claim 4 wherein $R^4$ is β-D-ribosyl.

7. A compound of claim 4 wherein $R^4$ is α-L-arabinosyl.

8. A compound of claim 4 wherein $R^4$ is β-D-chinovosyl.

9. A compound of claim 4 wherein $R^4$ is β-D-fucosyl.

10. A pharmaceutical composition which comprises an antifungal effective amount of a compound of claim 1 and a pharmaceutically acceptable vehicle.

* * * * *